United States Patent [19]

Bonse et al.

[11] 4,345,100
[45] Aug. 17, 1982

[54] PREPARATION OF α-KETOCARBOXYLIC ACID N-TERT.-BUTYLAMIDES

[75] Inventors: Gerhard Bonse, Cologne; Heinz U. Blank, Odenthal, both of Fed. Rep. of Germany

[73] Assignee: Bayer Aktiengesellschaft, Leverkusen, Fed. Rep. of Germany

[21] Appl. No.: 222,222

[22] Filed: Jan. 2, 1981

[30] Foreign Application Priority Data

Jan. 22, 1980 [DE] Fed. Rep. of Germany ....... 3002203

[51] Int. Cl.³ .......................................... C07C 102/08
[52] U.S. Cl. .................................... 564/124; 544/168; 546/245; 548/128; 548/236; 548/248; 548/255; 548/269; 548/324; 548/341; 548/378; 564/130; 548/530; 549/498
[58] Field of Search ................ 564/124, 130; 544/168; 548/341, 248, 236, 255, 269, 128, 324, 378; 546/245; 260/347.3, 326.43, 326.2

[56] References Cited

U.S. PATENT DOCUMENTS 2,518,156  8/1950  Magat .................................... 564/275
4,175,188 12/1979  Klenk et al. ......................... 544/182

FOREIGN PATENT DOCUMENTS 2733181  8/1979  Fed. Rep. of Germany .

OTHER PUBLICATIONS

Journal of American Chemical Society, vol. LXXIII, Jul.-Sep. 1951.
Journal of American Chemical Society, vol. LXXII, Sep.-Dec. 1950.
Journal of American Chemical Society, vol. LXXI, Sep.-Dec. 1949.
Journal of American Chemical Society, vol. LXX, Sep.-Dec. 1948.
H. Krauch and W. Kunr. Reaktionen des org. Chemie 1976, p. 544.
The Ritter Reaction, Chapter 3.
Ritter et al., J.A.C.S., 70 (1948), pp. 4045-4048.
Norris et al., J.A.C.S., 54 (1932), p. 2093.
Methodicum Chimicum 1974, vol. 6, p. 710.
Journal of the American Chemical Society, vol. LIV, May-Aug. 1932.

*Primary Examiner*—Arthur P. Demers
*Attorney, Agent, or Firm*—Sprung, Horn, Kramer & Woods

[57] ABSTRACT

A process for the preparation of an α-ketocarboxylic acid N-tert.-butylamide of the formula $$R-CO-CO-NH-C(CH_3)_3$$

in which
R is an aliphatic radical with up to 8 carbon atoms, a cycloalkyl radical with 3 to 6 carbon atoms, a phenyl or naphthyl radical or a heterocyclic radical, comprising reacting an acyl cyanide of the formula $$R-CO-CN$$

with tert.-butyl methyl ether of the formula $$(CH_3)_3C-O-CH_3$$

at a temperature between about 0° and 80° C. in the presence of an acid which is capable of activating the ether of formula (III) under the reaction conditions to give a tert.-butyl carbonium ion, and then hydrolyzing the reaction mixture. Advantageously the acyl cyanide is pivaloyl cyanide or benzoyl cyanide and is reacted with an approximately equimolar amount of the ether in the presence of about 1.1 to 1.5 times the molar amount of concentrated sulphuric acid as the activating acid. The products are useful as intermediates in the synthesis of known herbicides.

10 Claims, No Drawings

PREPARATION OF α-KETOCARBOXYLIC ACID N-TERT.-BUTYLAMIDES

The present invention relates to an unobvious process for the preparation of certain α-ketocarboxylic acid N-tert.-butylamides, which can be used as intermediate products for the synthesis of known herbicidal active compounds.

In general terms, α-ketocarboxylic acid amides are valuable intermediate products for the preparation of herbicidally active 1,2,4-triazin-5-one derivatives, which are readily available, for example according to DE-OS (German Published Specification) 2,165,554, from α-ketocarboxylic acid amides and hydrazine derivatives.

The reaction of secondary and tertiary alcohols, olefins or esters with nitriles in the presence of acids, for example sulphuric acid, or Lewis acids to give N-alkyl-substituted carboxylic acid amides has already been disclosed (see, for example, J. J. Ritter et al., J. Amer. Chem. Soc. 70, page 4,045 (1948).

This reaction (known in the literature as the "Ritter reaction") can be carried out with numerous aliphatic and aromatic mononitriles and dinitriles and with unsaturated nitriles and aldehyde cyanohydrins (see, for example, J. Amer. Chem. Soc. 71, page 4,128 (1949); 71, page 4,130 (1949); 72, page 5,577 (1950); and 73, page 4,076 (1951); and also "Organic Reactions", John Wiley & Sons, Inc. New York (1969), volume 17, pages 213–335; "Methodicum Chimicum", Georg Thieme Verlag Stuttgart (1974), volume 6, page 710; and "Reaktionen der Organischen Chemie" ("Reactions of Organic Chemistry") by H. Krauch and W. Kunz, Dr. Alfred Hüthig Verlag Heidelberg (1976), page (544).

It is furthermore known that acyl cyanides can also be used in the Ritter reaction in the same manner. Thus, the preparation of phenylglyoxylic acid N-tert.-butylamide in a yield of 72% of theory from benzoyl cyanide and tert.-butanol in the presence of Lewis acids is described, for example, in Acta Chem. Scand. 22, pages 1,787–1,790 (1968).

According to U.S. Pat. No. 4,175,188 and German Published Specification DOS 2,733,181, phenylglyoxylic acid N-tert.-butylamide and other glyoxylic acid N-tert.-butylamides can also be prepared, in yields of 54–95% of theory, by reacting the corresponding acyl cyanides with tert.-butanol or isobutylene, as components which form tert.-butylcarbonium ions, in the presence of strong acids (for example concentrated sulphuric acid), that is to say under the conditions of the Ritter reaction.

Alternative processes for the preparation of α-ketocarboxylic acids, such as for example, the addition of acid chlorides onto isonitriles (see, for example, Chem. Ber. 94, pages 1,116–1,121 (1961), or the oxidation of corresponding α-hydroxycarboxylic acid amides by means of heavy metal oxides (see, for example, German Published Specification DOS No. 2,208,568) require considerably more technical effort, as a result of the toxicity and the unpleasant odor of isonitriles or as a result of the toxicity and the high cost of heavy metal oxides.

However, it is desirable to improve the Ritter reaction such that the α-ketocarboxylic acid amides required can be obtained in a simple manner on an industrial scale by reacting readily available alcyl cyanides (see, for example, Agnew..Chem. 68, pages 425–435 (1965) with a suitable component which forms carbonium ions.

As is known from the literature, tert.-butylmethyl ether decomposes in the presence of sulphuric acid with the formation of isobutylene (see, J. Amer. Chem. Soc. 54, page 2,093 (1932). It is possible, according to U.S. Pat. No. 2,518,156, to prepare benzoic acid N-tert.-butylamide by reacting benzonitrile with tert.-butyl methyl ether (yield: 85% of theory).

According to the literature references J. Amer. Chem. Soc. 70, page 4,045 (1948), benzoic acid N-tert.-butylamide can even be prepared from benzonitrile and isobutylene in a yield of 90% of theory.

It has not hitherto been possible to infer from the state of the art industrial advantages in using tert.-butyl methyl ether instead of isobutylene or tert.-butanol as the source of tert.-butyl-carbonium ions in the Ritter reaction.

According to German Published Specification DOS 2,733,181, the reactants for the preparation of N-alkyl-substituted α-ketocarboxylic acid amides are employed in amounts such that more than the stoichiometric amounts of the alcohol or of the alkene, preferably 1.5–2 moles, are present per mole of the acyl cyanide. Investigations made by the applicants showed that only uneconomic yields of α-ketocarboxylic acid amides, such as trimethylpyruvic acid N-tert.-butylamide (yield <45% of theory) are obtained in a stoichiometric procedure according to the examples given in U.S. Pat. No. 4,175,188 and German Published Specification DOS 2,733,181.

The present invention now provides a process for the preparation of an α-ketocarboxylic acid N-tert.-butylamide of the general formula

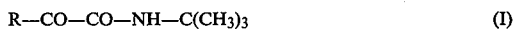

$$R-CO-CO-NH-C(CH_3)_3 \qquad (I)$$

in which
R represents an optionally substituted aliphatic radical with up to 8 carbon atoms, an optionally substituted cycloalkyl radical with 3 to 6 carbon atoms, an optionally substituted phenyl or naphthyl radical or an optionally substituted heterocyclic radical, characterized in that an acyl cyanide of the general formula

$$R-CO-CN \qquad (II)$$

wherein
R has the meaning indicated above, is reacted with tert.-butyl methyl ether of the formula

$$(CH_3)_3C-O-CH_3 \qquad (III)$$

at a temperature between 0° and 80° C. in the presence of an acid which is capable of activating the ether of formula (III) under the reaction conditions to give a t-butyl-carbonium ion, and optionally in the presence of a solvent or solubilizing agent, and the reaction mixture is then hydrolyzed. The process of the present invention provides compounds of formula (I) in high yields and in high purity.

The reaction according to the invention is carried out under the conditions of the abovementioned "Ritter reaction". It is particularly surprising that, in particular when approximately stoichiometric batches are used in each case, considerably higher yields can be achieved with the aid of the reaction according to the invention than when t-butanol or isobutylene is used as the source of t-butyl-carbonium ions.

If, in addition to t-butyl methyl ether, pivaloyl cyanide is used as the starting substance and the reaction is carried out in the presence of concentrated sulphuric acid, the course of the reaction can be represented by the following equation:

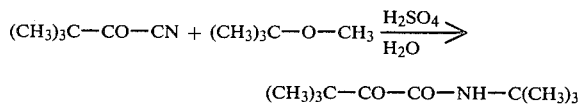

$$(CH_3)_3C-CO-CO-NH-C(CH_3)_3$$

Particularly preferred acyl cyanides of formula (II) to be employed as starting substances for the process of the present invention are those in which R represents a straight-chain or branched alkyl radical with 1 to 4 carbon atoms which is optionally substituted by a substituent selected from alkoxy with 1 to 4 carbon atoms, carbalkoxy with 1 to 4 carbon atoms in the alkoxy group, nitro, nitrile and/or halogen (for example, fluorine, chlorine, bromine or iodine), represents a cycloalkyl radical which has 5 or 6 carbon atoms in the ring system and is optionally substituted by a substituent selected from alkyl, alkoxy or carbalkoxy with in each case up to 4 carbon atoms, nitro and/or halogen (for example, fluorine, chlorine or bromine), represents a phenyl or naphthyl which is optionally substituted by a substituent selected from alkyl, alkoxy or carbalkoxy with in each case up to 4 carbon atoms, nitro and/or halogen (for example, fluorine, chlorine or bromine) or represents a 5-membered or 6-membered heterocyclic radical which can contain 1 to 3 hetero-atoms, such as oxygen, sulphur and/or nitrogen, in the ring and can also be fused to a benzene ring and is optionally substituted by a substituent selected from alkyl, alkoxy or carbalkoxy with in each case up to 4 carbon atoms, nitro, nitrile and/or halogen (for example, fluorine, chlorine or bromine). Examples of heterocyclic radicals which are particularly suitable as radicals R are: morpholinyl, imidazolyl, pyrazolyl, pyrrolyl, isoxazolyl, piperidinyl, oxazolyl, 1,2,4-triazol-1-yl, 1,2,4-triazol-4-yl, 1,2,3-triazolyl, 1,2,4-thiadiazol-2-yl, benzimidazolyl and furanyl.

Some of the acyl cyanides of the formula (II) are known; acyl cyanides which are not yet known can be prepared by known processes (see Agnew. Chem. 68. pages 425–435 (1965); and also U.S. Patent Applications 967,932, filed Dec. 8, 1978; 967,934, filed Dec. 8, 1978; U.S. Pat. No. 4,143,068 and German Published Specifications DOS 2,708,182 and 2,708,183).

Pivaloyl cyanide ((CH$_3$)$_3$C—CO—CN) and benzoyl cyanide (C$_6$H$_5$CO—CN) may be mentioned as particularly preferred acyl cyanides of formula (II) for use in the process of the present invention.

Tert.-butyl methyl ether of formula (III) can be obtained on a large industrial scale and is commercially available.

The reaction according to the invention is carried out in the presence of an acid which is capable of activating the ether of formula (III) under the reaction conditions to give a t-butyl-carbonium ion.

Possible acids of this type are, in particular, concentrated sulphuric acid and also a number of other acids customary in Ritter reactions, in particular certain sulphonic acids, phosphonic acids and halogenoalkanecarboxylic acids, of which the following may be mentioned specifically: (a) sulphonic acids (for example methanesulphonic acid, ethanesulphonic acid, propanesulphonic acid, butanesulphonic acid, trifluoromethanesulphonic acid, benzenesulphonic acid, toluenesulphonic acid, benzylsulphonic acid, 4-(2-dodecyl)-phenylsulphonic acid, hexadecylsulphonic acid, octadecylsulphonic acid, benzene-1,3-disulphonic acid, ethane-1,2-disulphonic acid and butane-1,4-disulphonic acid); (b) aliphatic and aromatic phosphonic acids (for example methanephosphonic acid, ethanephosphonic acid, phenylphosphonic acid, benzylphosphonic acid and ethane-1,2-diphosphonic acid) and (c) halogenoalkanecarboxylic acids (for example dichloroacetic acid, trichloroacetic acid, trifluoroacetic acid and perchloropropionic acid).

It is possible to carry out the reaction according to the invention in the presence of one or more such acids.

The reaction temperature can be selected within the substantial range as indicated above, of between about 0° and 80° C., preferably between about 10° and 40° C. It is expedient to carry out the subsequent hydrolysis by means of ice-water.

The reaction is in general carried out under normal pressure.

The reaction can be carried out in the absence or in the presence of a solvent or solubilizing agent. Possible solubilizing agents are certain organic solvents; particularly suitable solvents are glacial acetic acid and methylene chloride, but dialkyl ethers (such as diethyl ether or di-isopropyl ether) and diaryl ethers (such as diphenyl ether) may also be mentioned. However, it may also be appropriate to add excess t-butyl methyl ether of formula (III) as the solvent and then to carry out the reaction without an additional solubilizing agent.

In carrying out the process according to the invention, unless a considerable excess of t-butyl methyl ether of formula (III) is used as the solvent, in general 1 to 1.5 moles of t-butyl methyl ether, preferably 1 to 1.2 moles of t-butyl methyl ether, are employed per mole of acyl cyanide of the formula (II); the stoichiometric molar ratio of 1 mole of t-butyl methyl ether to 1 mole of an acyl cyanide of the formula (II) is particularly preferred. If the t-butyl methyl ether is to serve as the solvent at the same time, this can be employed in virtually any desired excess, as can other solvents.

The acids required for carrying out the process according to the invention are employed in the stoichiometric amount or in an amount greater than the stoichiometric amount. In general, 1 to 5 moles, preferably 1.1 to 1.5 moles, of acid are employed per mole of acyl cyanide of the formula (II).

In carrying out the process, it is appropriate to follow a procedure in which the acid or a mixture of solvent and acid is intially introduced into the reaction vessel and a mixture of the two other components, that is to say the acyl cyanide and t-butyl methyl ether, optionally in a solvent, is added.

The reaction times are in general 1 to 10 hours. The hydrolysis is most appropriately carried out by subsequently pouring the reaction mixture onto ice. The α-ketocarboxylic acid amides formed can be isolated by filtration or by extraction.

Extraction agents which are suitable here are solvents which are not miscible with water in all proportions, for example ethers (such as diethyl ether or diisopropyl ether), esters (such as ethyl acetate), ketones (such as methyl isobutyl ketone), halogenated hydrocarbons (such as methylene chloride, chlorobenzene or dichlorobenzene), and furthermore aromatic compounds (such as benzene, toluene, o-xylene, ethylbenzene, cumene or nitrobenzene). Methylene chloride is preferably used. It is also possible for excess tert.-butyl methyl ether of formula (III) which has been employed as the solvent and has not entered into the reaction to be used at the same time as the extraction agent during working up; this can be re-used after distillation.

Some of the α-ketocarboxylic acid amides of the formula (I) which can be prepared according to the invention are known; they can be used, for example, as intermediate products for the synthesis of herbicidally active compounds. Thus, for example, the compound 4-amino-6-tert.-butyl-3-methylthio-1,2,4-triazin-5(4H)-one of formula (VI) which is particularly herbicidally active is obtained from trimethylpyruvic acid N-tert.-butylamide of formula (Ia) in accordance with the following equation (see German Patent Specification No. 1,795,784):

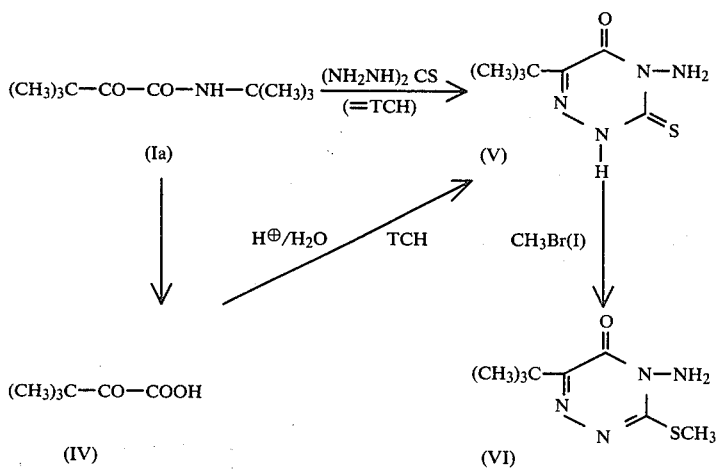

Trimethylpyruvic acid N-tert.-butylamide of formula (Ia) can be subjected, either direct or after prior hydrolysis in an aqueous hydrohalic acid solution to give the free α-keto acid of formula (IV), to a condensation reaction in a known manner, with 1 to 1.5 moles of thiocarbohydrazide, NH₂—NH—CS—NH—NH₂ (=TCH), at temperatures between 20° and 100° C., to give 4-amino-6-tert.-butyl-3-mercapto-1,2,4-triazin-5(4H)-one of formula (V), which can be methylated by means of a methyl halide (for example methyl iodide or methyl bromide), in alkaline solution to give the product of formula (VI) (see Chem. Ber. 97, pages 2,173-8 (1964); German Published Specifications 2,165,554 and 2,648,300, and U.S. Pat. Nos. 4,113,767 and 4,175,188).

The preparative Examples 1(a) and 2(a) which follow illustrate the process according to the present invention in more detail.

PREPARATIVE EXAMPLES

EXAMPLE 1

(a) (CH₃)₃C—CO—CO—NH—C(CH₃)₃

This example illustrates a preferred procedure according to the invention:

27.8 (0.25 mole) of pivaloyl cyanide, dissolved in 22 g (0.25 mole) of t-butyl methyl ether were added to a reaction mixture, which had been initially introduced into the reaction vessel, consisting of 37.5 g of concentrated sulphuric acid and 52.5 g of glacial acetic acid at 20° to 30° C. in the course of 30 minutes. After subsequently stirring the reaction mixture at room temperature for 2 hours, it was poured onto 125 g of ice and stirred thoroughly. The product which precipitated was filtered off, washed with water and dried. 40.8 g (87.5% of theory) of analytically pure trimethylpyruvic acid N-tert.-butylamide with a melting point of 65° C. and a content of >99% (determined by gas chromatography) were obtained.

Comparison Examples (b) The following Comparison Example illustrates a procedure corresponding to the state of the art, such as is described, for example, in Example 1 of U.S. Pat. No. 4,175,188. However, for the purpose of comparison with Example 1(a), according to the invention, described above, a stoichiometric amount of the source of carbonium ions, that is to say t-butanol, was reacted with pivaloyl cyanide.

27.8 g (0.25 mole) of pivaloyl cyanide were added to a mixture of 18.5 g (0.25 mole) of t-butanol and 12.5 ml of methylene chloride. 37.5 g of 98% strength sulphuric acid were then added dropwise at 0° to 5° C., while stirring, and the mixture was then warmed to 20° C. After subsequently stirring for 4 hours, the reaction mixture was poured onto 100 g of ice and stirred for a further 30 minutes. It was then diluted with 75 ml of methylene chloride, the organic phase was separated off and the methylene chloride solution was evaporated. 47.0 g of a yellow oily product remained, in which the content of the desired trimethylpyruvic acid N-tert.-butylamide was 33% (determined by gas chromatography), so that a yield of 33.5% of theory resulted. (c) The following Comparison Example shows a procedure corresponding to the state of the art, such as is described, for example, in Example 3 of German Published Specification DOS 2,733,181. As in Comparison Example 1(b), a stoichiometric amount of the source of carbonium ions employed in this case, that is to say isobutylene, was reacted with pivaloyl cyanide.

27.8 g (0.25 mole) of pivaloyl cyanide were reacted with 14 g (0.25 mole) of isobutylene, as described in Example 3 of German Published Specification DOS 2,733,181, in a stirred apparatus affording protection from moisture. 20.4 g of crude trimethylpyruvic acid N-tert.-butylamide with a content of 93.8% (determined by gas chromatography) were obtained, which corresponded to a yield of 41.3% of theory. (d) The procedure followed was as in Comparison Example 1(c), but the working up of the mixture obtained in the stoichiometric reaction of pivaloyl cyanide with isobutylene was carried out as described in Example 1(b), of U.S. Pat. No. 4,175,188.

22.0 g of crude trimethylpyruvic acid N-tert.-butylamide with a content of 93.5% (determined by gas chromatography) were obtained, which corresponded to a yield of 44.4% of theory.

EXAMPLE 2

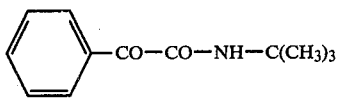
(a)

This example illustrates a preferred procedure according to the invention.

32.8 g (0.25 mole) of benzoyl cyanide, dissolved in 22 g (0.25 mole) of t-butyl methyl ether were added to a reaction mixture, which had been initially introduced into the reaction vessel, consisting of 37.5 g of concentrated sulphuric acid and 52.5 g of glacial acetic acid at 20° to 30° C. in the course or 30 minutes. After subsequently stirring the reaction mixture at room temperature for 2 hours, it was poured onto 125 g of ice and stirred thoroughly. The product which precipitates was filtered off, washed with water and dried. 45.6 g (88.9% of theory) of analytically pure phenylglyoxylic acid N-tert.-butylamide with a melting point of 78° C. and a content of >99% (determined by gas chromatography) were obtained.

Comparison Examples (b) The following Comparison Example shows a procedure corresponding to the state of the art, such as is described, for example, in Example 1 of German Published Specification DOS 2,733,181, in which, however, t-butanol was reacted with a stoichiometric amount of benzoyl cyanide:

37.1 g of phenylglyoxylic acid N-tert.-butylamide with a content of 91.6% (determined by gas chromatography) were obtained, which corresponded to a yield of 66.2% of theory. (c) The procedure followed was as described in Example 3 of German Published Specification DOS 2,733,181, but isobutylene was reacted with a stoichiometric amount of benzoyl cyanide.

26.9 g of phenylglyoxylic acid N-tert.-butylamide with a content of 90.8% (determined by gas chromatography) were obtained, which corresponded to a yield of 47.6% of theory.

It will be understood that the sepcification and examples are illustrative but not limitative of the present invention and that other embodiments within the spirit and scope of the invention will suggest themselves to those skilled in the art.

We claim:

1. A process for the preparation of an -ketocarboxylic acid N-tert.-butylamide of the formula

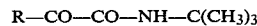

in which
R is an aliphatic radical with up to 8 carbon atoms, a cycloalkyl radical with 3 to 6 carbon atoms, a phenyl or naphthyl radical or a morpholinyl, imidazolyl, pyrazolyl, pyrrolyl, isoxazolyl, piperidinyl, oxazolyl, 1,2,4-triazol-1-yl, 1,2,4-triazol-4-yl, 1,2,3-triazolyl, 1,2,4-thiadiazol-2-yl, benzimidazolyl or furanyl radical, comprising reacting an acyl cyanide of the formula

with an approximately equimolar amount of tert.-butyl methyl ether of the formula

at a temperature between about 0° and 80° C. in the presence of an acid which is capable of activating the ether of formula (III) under the reaction conditions to give a tert.-butyl-carbonium ion, and then hydrolyzing the reaction mixture.

2. A process according to claim 1, wherein the reaction is carried out at a temperature between about 10° and 40° C.

3. A process according to claim 1, wherein the acyl cyanide and tert.-butyl methyl ether are reacted in a molar ratio of about 1:1 to 1:1.5.

4. A process according to claim 1, wherein about 1 to 5 moles of acid are employed per mole of acyl cyanide.

5. A process according to claim 1, wherein the acid is concentrated sulphuric acid.

6. A process according to claim 1, wherein the acyl cyanide is pivaloyl cyanide.

7. A process according to claim 1, wherein the acyl cyanide is benzoyl cyanide.

8. A process according to claim 1, wherein the reaction between the acyl cyanide and the ether is carried out in the presence of a solvent or solubilizing agent.

9. A process according to claim 1, wherein the reaction between the acyl cyanide and the ether is carried out in the presence of glacial acetic acid or methylene chloride.

10. A process according to claim 9, wherein the reaction is carried out at a temperature between about 10° and 40° C., the acyl cyanide is pivaloyl cyanide or benzoyl cyanide and is reacted with the ether in the presence of about 1.1 to 1.5 times the molar amount of concentrated sulphuric acid as the activating acid.

* * * * *

UNITED STATES PATENT AND TRADEMARK OFFICE
CERTIFICATE OF CORRECTION

PATENT NO. : 4,345,100
DATED : Aug. 17, 1982
INVENTOR(S) : Gerhard Bonse et al

It is certified that error appears in the above—identified patent and that said Letters Patent is hereby corrected as shown below:

Column 8, line 4, Insert --α-- before "-ketocarboxylic".

Signed and Sealed this

Twenty-eighth Day of December 1982

[SEAL]

Attest:

GERALD J. MOSSINGHOFF

Attesting Officer

Commissioner of Patents and Trademarks